United States Patent [19]

Laurence

[11] Patent Number: 4,665,032

[45] Date of Patent: May 12, 1987

[54] HUMAN T CELL HYBRIDOMAS WHICH PRODUCE IMMUNOSUPPRESSIVE FACTORS

[75] Inventor: Jeffrey C. Laurence, New York, N.Y.

[73] Assignee: Cornell Research Foundation, Inc., Ithaca, N.Y.

[21] Appl. No.: 625,431

[22] Filed: Jun. 28, 1984

[51] Int. Cl.$^4$ .................. C12N 5/00; C12N 15/00; C12R 1/91

[52] U.S. Cl. .................. 435/240; 435/68; 435/172.2; 435/948; 935/101; 530/380

[58] Field of Search .................. 435/7, 68, 240, 241, 435/172.2, 948; 424/85, 101; 436/548; 260/112 R; 935/101, 109; 530/380

[56] References Cited

U.S. PATENT DOCUMENTS 4,544,632 10/1985 Yamamura et al. .................. 435/68

FOREIGN PATENT DOCUMENTS 2108528 5/1983 United Kingdom ............. 435/172.2

OTHER PUBLICATIONS

Irigoyen et al., "Generation of Functional Human T Cell Hybrids", *J. Exp. Med.,* vol. 154, 1981, pp. 1827-1837.

Grillot-Courvalin et al., "Establishment of a Human T-Cell Hybrid Line with Suppressive Activity", *Nature,* vol. 292, Aug. 27, 1981, pp. 844 and 845.

Laurence, J., "The Immune System in AIDS", *Scientific American,* vol. 253, No. 6, Dec. 1985, pp. 84-93.

Laurence, J. et al., "Immunoregulatory Lymphokines of T Hybridomas from AIDS Patients: Constitutive and Inducible Suppressor Factors", *Science,* vol. 225, Jul. 6, 1984, pp. 66-68.

Laurence, J. et al., "Lymphadenopathy-Associated Viral Antibody in AIDS", *The New England Journal of Medicine,* V. 311, N. 20, Nov. 15, 1984, pp. 1269-1273.

Joller-Jemelka, H. I. et al., "Immunologishe Laboruntersuchungen bei Patienten mit Erworbenem Immunmangelsyndrom (AIDS) und bei AIDS-Verdacht", Schweiz. med. Wschr., V. 115, (1985), pp. 125-132.

Laurence, J. et al, "Soluble Suppressor Factors in Patients with AIDS . . . ", J. Clin. Invest., vol. 72, pp. 2072-2081, 1983.

Shohat, B. et al., "Serum Suppressor Factor in Patients with AIDS . . . ", First Annual. Conf. Medical Research, Petah Tikva, Israel, May 23, 1984.

Greene, W., "Production of Human Suppressor T Cell Hybridomas", J. of Immunology, vol. 129, No. 5, pp. 1986-1992, 1982.

Grillot-Courvalin et al, "Establishment of Human T-Cell Hybrid Line with Suppressive Activity", Nature, vol. 292, pp. 844-845, 1981.

*Primary Examiner*—Blondel Hazel
*Assistant Examiner*—Elizabeth C. Weimar
*Attorney, Agent, or Firm*—Sughrue, Mion, Zinn, Macpeak & Seas

[57] ABSTRACT

A human T cell hybridoma comprising the product of:
(A) fusion of:
  (i) a T cell from a patient with ARC or AIDS, wherein said T cell secretes an SSF capable of specifically inhibiting T cell-dependent responses while leaving other immune functions intact, and
  (ii) a human T cell line, followed by (B) selection from the product of (A) of a human T cell hybridoma which secretes an SSF capable of specifically inhibiting T cell-dependent responses while leaving other immune functions intact.

8 Claims, 3 Drawing Figures

HUMAN T CELL HYBRIDOMAS WHICH PRODUCE IMMUNOSUPPRESSIVE FACTORS

This invention was made with Government support under NIH Grant No. CA 35018-01 and the American Heart Association 80-423. The United States of America has certain rights to this invention.

FIELD OF INVENTION

The present invention relates to human T cell hybridoma cell lines which produce immunosuppressive factors that specifically inhibit T cell-mediated immune responses.

BACKGROUND OF THE INVENTION

Acquired immune deficiency syndrome (hereinafter "AIDS") is defined as a disease in an individual less than 60 years of age characteristic of a defect in cell-mediated immunity which arises in a person without known predisposition for diminished resistance (see *Morbidity and Mortality Weekly Report* 31:507 (1982)). The common denominator of patients with AIDS is a profound but selective abnormality of immunoregulation manifest by susceptibility to opportunistic infections and malignancies (e.g., Kaposi's sarcoma) characteristic of certain genetic and iatrogenic immune deficiencies (see Fauci, A. S., *Ann. Intern. Med.* 100:92 (1984) and Gottlieb, M. S., *Ann. Intern. Med.* 99:208 (1983)). Virtually all individuals having AIDS show a deficiency in cellular immune responses (see Masur, H. M., Michelis, M. A., Greene, J. R., Onorato, I., Vande Stouwe, R. A., Holzman, R. S., Wormser, G., Brettman, L., Lange, M., Murray, H. W., and Cunningham-Rundles, S., *N. Engl. J. Med.* 305:1431 (1981) and Gottlieb, M. S., Schroff, R., Schanker, H. M., Weisman, J. D., Fan, P. T., Wolf, R. A., and Saxon, A., *N. Engl. J. Med.* 305:1426 (1981)).

Most patients with AIDS give a history of nonspecific complaints lasting from two to eight months or more. Dr. Thomas Quinn of the National Institute of Allergy and Infectious Diseases has suggested that the term "AIDS-related complex" (hereinafter "ARC") be used to describe such individuals with prodromal or "pre-AIDS". A diagnosis of ARC is based upon the occurrence of a combination of clinical findings and laboratory abnormalities, listed below and fully described in Krause, R. M., *Rev. Infect. Dis.* 6:270 (1984).

| Diagnosis of ARC | |
|---|---|
| Two clinical findings plus | Two laboratory abnormalities |
| Fever > 3 months | ↓ T-helper cells |
| Weight loss > 10 percent BWT* | ↓ T-helper/T-suppressor ratio |
| Lymphadenopathy, 3 months | ↑ Serum globulins |
| Diarrhea | ↓ Blastogenesis |
| Fatigue | Anergy |
| Night sweats | |

*BWT = body weight total.

It has been demonstrated that supernatants from lectin-free cultures of peripheral blood mononuclear cells (hereinafter "PBMC") obtained from certain homosexual males with AIDS or ARC contain soluble suppressor factors (hereinafter "SSF") which inhibit (i) spontaneous and pokeweed mitogen-derived B cell differentiation into plasmacytes, and (ii) T cell blastogenic responses to antigen (see Laurence, J., Gottlieb, A. B. and Kunkel, H. G., *J. Clin. Invest.* 72:2071 (1983)). These SSF are the product of the interaction of T cells with adherent normal cells. An adherent cell as used herein is a mononuclear cell identified as a monocyte (a) by its capacity to bond to a plastic surface; (b) by not possessing B or T-cell surface markers, i.e., surface immunoglobulin and E-rosetting capacity; and (c) by its ability to be tagged by antibody 63D3 which is a monoclonal antibody against human monocytes (Becton-Dickenson, California). That is, T cells or T cell derived factors from ARC or AIDS patients (hereinafter collectively "AIDS patients"), but not from healthy homosexual or heterosexual controls, or heterosexual individuals with Epstein-Barr virus or cytomegalovirus mononucleosis, can interact with adherent normal cells in the formation of SSF (see Laurence, J., Gottlieb, A. B. and Kunkel, H. G., *J. Clin. Invest.* 72:2071 (1983)).

Human T cell hybridomas secreting molecules able to interfere with T cell-directed polyclonal immunoglobulin synthesis independent of T cell mitogenesis (see Grillot-Courvalin, C., Dellagi, K., Chevalier, A. and Brouet, J. C., *J. Immunol.* 129:1008 (1982) and Grillot-Courvalin, C. and Brouet, J. C. *Nature* 292:844 (1982)), or with antibody production directly at the level of the B cell (see Greene, W. C., Fleisher, T. A., Nelson and D. L., Waldmann, T. A., *J. Immunol.* 129:1986 (1982), have been described. These studies utilized PBMC from healthy individuals enriched for activated suppressor T cells by in vitro exposure to concanavalin A (see Greene, W. C., Fleisher, T. A., Nelson, D. L. and Waldmann, T. A., *J. Immunol.* 129:1986 (1982)), or unstimulated T cells from patients with common variable hypogammaglobulinemia (see Grillot-Courvalin, C., Dellagi, K., Chevalier, A. and Brouet, J. C., *J. Immunol.* 129:1008 (1982) and Grillot-Courvalin, C. and Brouet, J. C., *Nature* 292:844 (1982) and Depper, J. M., Leonard, W. J., Black, R. M., Waldmann, T. A. and Greene, W. C., *Clin. Res.* 30:346A (1982)). These T cell hybridomas only secrete non-specific suppressor factors, i.e., the suppressor factors do not specifically inhibit T cell-dependent immune responses. Further, there is no evidence that these non-specific suppressor factors have in vivo efficacy as immunosuppressive agents. In addition, all of the above-described hybridomas are constitutive producers of suppressor factors, i.e., the production of these suppressor factors by the hybridomas is not controllable.

Soluble immune response suppressor factors from several murine T cell hybridomas have been recovered and thus demonstrate that a continuous microphage cell line can be employed to process or generate soluble immune reponse suppressor factors under the direction of T lymphokines (see Aune, T. W. and Pierce, C. W., *Proc. Nat'l Acad. Sci.* 78:5099 (1981)).

At least two soluble immune response suppressor factors have been identified in man (see Fleisher, T. A., Greene, W. C., Blaese, R. M. and Waldmann, T. A., *J. Immunol.* 126:1192 (1981)) and Greene, W. C., Fleisher, T. A. and Waldmann, T. A., *J. Immunol.* 126:1185 (1981)), one of which has been produced by a continuous T cell line (Greene, W. C., Fleisher T. A. and Waldmann, T. A., *J. Immunol.* 126:1185 (1981)). SSF from AIDS patients, as well as SSF from the T cell hybridomas of the present invention, are distinguishable from the above-described factors by the restriction of activity to T cell-dependent processes, and the lack of susceptibility to effects thereon of specific sugars. The activity of the known suppressor factors described above can be specifically inhibited by high concentrations, i.e., greater than 50 mM, of sugars such as L-rhamnose, α-methylmannoside, L-fucose, and N-acetyl-D-glucosamine.

SUMMARY OF THE INVENTION

An object of the present invention is to provide a T cell hydridoma which secretes a specific soluble suppressor factor, i.e., an SSF capable of profoundly yet specifically inhibiting T cell-dependent immune responses, while leaving intact other immune functions, including polyclonal T cell-independent B cell responses, monocyte activity, and natural killer T cell reactivity.

Another object of the present invention is to provide T cell hybridomas which secrete SSF for facilitating the investigation of T lymphokine-dependent inhibitory phenomena and which permit direct comparisons with products isolated in other disorders linked to cell or factor mediated immunosuppression.

A still further object of the present invention is to provide T cell hybridomas which secrete SSF which can be useful in the management of disorders requiring immunosuppression, such as autoimmune diseases, hypersensitivity reactions, and in preparation for organ allografting.

The above objects of the present invention have been met by a human T cell hybridoma comprising: the product of:

(a) fusion of:
 (i) a T cell from a patient with ARC or AIDS, wherein said T cell secretes an SSF capable of specifically inhibiting T cell-dependent responses while leaving other immune functions intact, and
 (ii) a human T cell line,
followed by
(B) selection from the product of (A) of a human T cell hybridoma which secretes an SSF capable of specifically inhibiting T cell-dependent responses while leaving other immune functions intact.

DETAILED DESCRIPTION OF THE INVENTION

Figure 1:
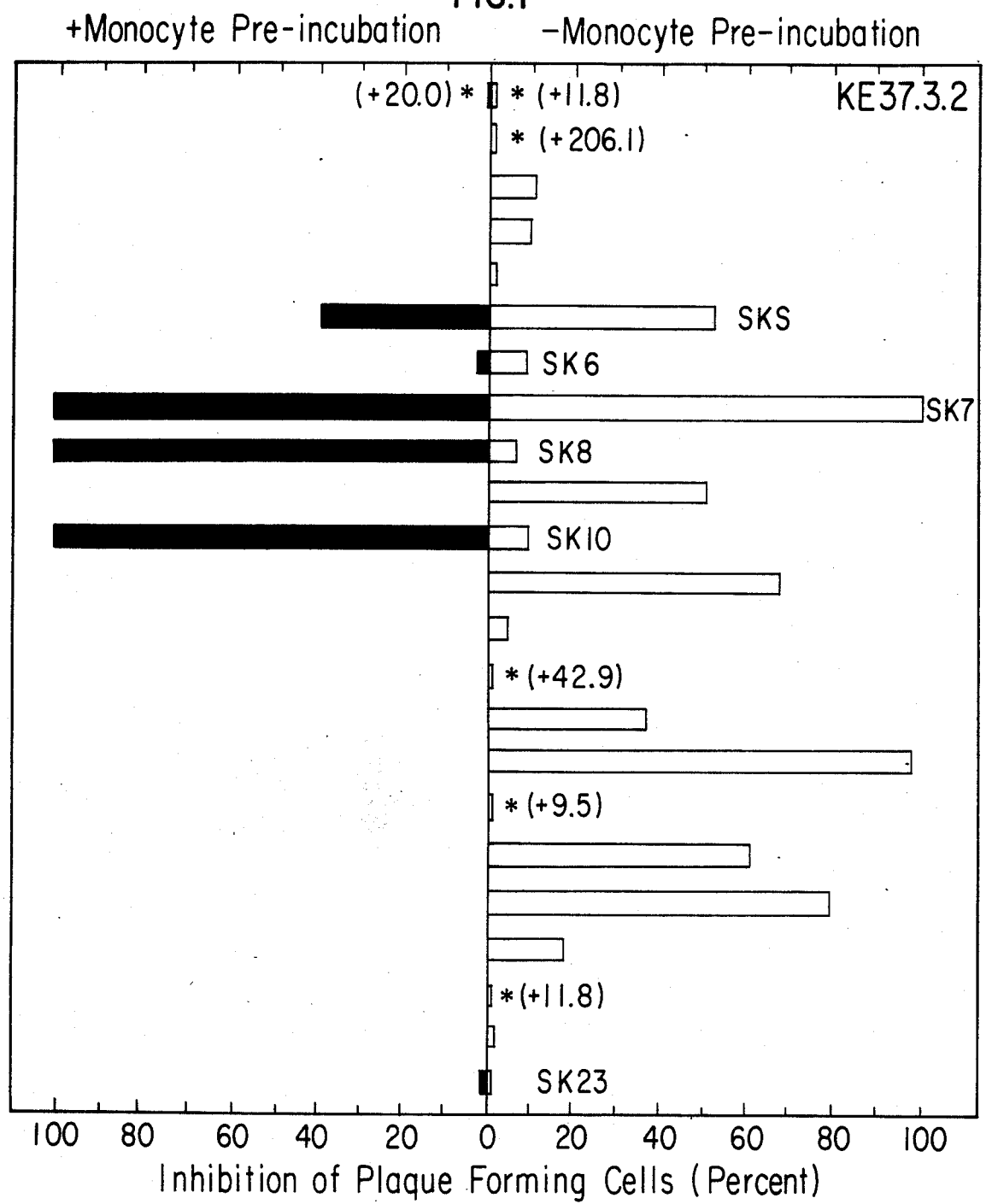
FIG. 1 illustrates the effect of SSF obtained from T cell hybridomas of the present invention on T cell-dependent polyclonal immunoglobulin synthesis.

As stated above, the present invention relates to a human T cell hybridoma comprising: the product of:
(A) fusion of:
 (i) a T cell from a patient with ARC or AIDS, wherein said T cell secretes an SSF capable of specifically inhibiting T cell-dependent responses while leaving other immune functions intact, and
 (ii) a human T cell line;
followed by
(B) selection from the product of (A) of a human T cell hybridoma which secretes an SSF capable of specifically inhibiting T cell-dependent responses while leaving other immune functions intact.

As used herein, the expression "T cell-dependent immune responses" includes: in vitro pokeweed mitogen-induced polyclonal production and phytohemagglutinin-stimulated blastogenesis. Further, as used herein, the expression "T cell-independent immune responses" includes: in vitro Epstein-Barr virus-induced polyclonal antibody production; natural killer T cell activity; monocyte-mediated bacteria and parasite killing; and peroxidase production by monocytes.

The T cells employed in producing the hybridomas of the present invention are isolated from PBMC obtained from any patient with ARC or AIDS wherein the PBMC secrete SSF. The T cells are isolated by well known means as described in Laurence, J., Gottlieb, A. B. and Kunkel, H. G., *J. Clin. Invest.* 72:2071 (1983) and detailed in Example 1 below.

The isolated T cells are then fused to any of a number of widely available mutagenized or non-mutagenized human T cell lines. As used herein, the expression "mutagenized human T cell lines" refers to human T cell lines which have been mutagenized such that they are no longer capable of growing in the presence of culture media containing selective agents, e.g., hypoxanthine, aminopterin, and thymidine (hereinafter "HAT"). That is, in the presence of a HAT-containing culture medium, the mutagenized human T cell lines are not able to grow, and only the hybridoma cells are able to grow, i.e., are HAT resistant. The isolated T cells would also not survive since they do not have the ability for constitutive growth. In this manner, selection of hybridomas can be achieved by growth in a medium containing selective agents.

As used herein, the expression "non-mutagenized human T cell lines" refers to human T cell lines which, for example, lack a cell surface marker found in certain human T cells. That is, for example, the T cell line MOLT-4 lacks the cell surface marker OKT4. The fused cells would possess the OKT4 cell surface marker from the isolated T cells. Again, the isolated T cells would not survive since they do not have the ability for constitutive growth. Hybribomas can then be selected by tagging the hybridomas with OKT4 antibodies of mouse origin and empolying an indirect rosetting technique using goat-anti-mouse-immunoglobulin-coated ox erythrocytes for binding to the OKT4 antibodies as described in Mayer, L., Fu, S. M., Kunkel, H. G., *J. Exp. Med.* 156:1860 (1982) and Mayer, L. Kunkel, H. G., *Lymphokine Res.* 3:107 (1984).

Examples of mutagenized human T cell lines which can be employed in the present invention include KE 37.3.2, a hypoxanthine-guanine phosphoribosyl transferase-deficient mutant of the human T acute lymphoblastic leukemia line KE 37 and Jurkat 3, a hypoxanthine-guanine phosphoribosyl transferase-deficient mutant of the human T cell lymphoma line Jurkat (see Mayer, L., Fu, S. M. and Kunkel, H. G., *J. Exp. Med.* 156:1860 (1982)). Examples of non-mutagenized human T cell lines which can be employed in the present invention include KE 37, MOLT 4 (ATCC No. CRL 1582), MOLT 3 (ATCC No. CRL 1552), CCRF-CEM (ATCC No. CCL 119) and HuT 78 (ATCC No. TIB 161).

Regardless of the human T cell line employed, i.e., whether mutagenized or non-mutagenized, for fusion with T cells from an AIDS patient, the fusion technique is identical. Fusion can be mediated by any of the well-known cell-cell-fusion agents such as polyethylene glycol, Sendai virus, or latex beads, as is well known in the art and described in Irigoyen, O., Rizzolo, P. V., Thomas, Y., Rogozinski, L. and Chess, L. *J. Exp. Med.*, 154:1827 (1981); Grillot-Courvalin, C., Brouet, J. C., Berger, R. and Berheim, A., *Nature* 292:844 (1981); Okada, M., Yoshimura, N., Kaieda, T., Yamamura, Y. and Kishimoto, T., *Proc. Natl. Acad. Sci. USA* 78:7717 (1981); and *T Cell Hybridomas*, Boehmer, H. V., Haus, W., Kohler, G., Melchers, F. and Zeuthen, J., Eds., Springer-Verlag, Berlin (1982), the disclosures of which are herein each independently incorporated by reference.

More specifically, the T cells from an AIDS patient are stimulated with a T cell mitogen, for example, concanavalin A, in order to prepare T cells which have an increased fusion efficiency when compared to unstimulated T cells. These cells are then mixed with the human T cell line in the presence of a fusion agent so that exchange of genetic material following cell-cell contact is realized. The fusion agent is then removed from the system by washing, and the hybridomas are selected using, for example, selection medium or the resetting technique as described above and detailed in Example 1 and Example 2, respectively.

Several human T cell hybridomas have been obtained in accordance with the present invention as described in Examples 1 and 2 below. Four of such hybridomas, i.e., SK 7, SK 8, HM 1 and HM 2 have been deposited at the American Type Culture Collection and have the identifying characteristics of ATCC Nos. HB8584, HB8585, HB8586 and HB8587, respectively. SK 7 and SK 8 were derived from T cells obtained from a patient who fulfills all of the criteria for a diagnosis of ARC. HM 1 and HM 2 were derived from T cells obtained from a patient who fulfills all of the criteria for a diagnosis of AIDS.

The types of clinical diseases and syndromes in man for which SSF are believed to have clinical efficacy include: the preparation for organ and tissue allotransplantation and treatment of aggressive autoimmune disorders and severe hypersensitivity reactions. Specific examples include: rheumatoid arthritis, systemic lupus erythematosus, severe insulin-dependent diabetes mellitus, inflammatory bowel diseases, and graft versus host disease. Another example would be as an anti-proliferative agent, i.e., in the therapy of T cell cancers.

An appropriate dose of SSF, administered either orally, subcutaneously or intravenously, which would be effectively immunosuppressive in humans can be determined from: (a) the murine model detailed in Section H below; and (b) extrapolation from data with the immunosuppressive agent cyclosporin A, for which equivalent immunosuppressive doses in mouse and man have been established (Britton, S. and Palacios, R., *Immunol. Rev.*, 65:5 (1982)). In this manner, the equivalent of 50 ml of SF 7 hybridoma supernatant, which could be concentrated to a volume of 5.0 ml by standard ultrafiltration techniques, would be appropriate for administration daily to a 70 kg by body weight individual to achieve the desired effects.

The following examples are provided to illustrate the present invention in greater detail and are not in any way intended to be construed as limiting the scope of the present invention.

EXAMPLE 1

A.

Preparation of Stimulated T Cells

In this Example, T cells from a homosexual male (hereinafter "patient SEL") with unexplained generalized lymphadenopathy, persistent fever, malaise, high titers of SFF, and high titers of an antibody to the AIDS-linked retrovirus (lymphadenopathy-associated virus, i.e., LAV) as detected by ELISA to the internal antigen p25 (see Baree-Sinoussi, Chermann, J. C. and Rey, F., *Science* 220:868 (1983)) were employed as described in detail below. Patient SEL was diagnosed as an ARC patient by the criteria discussed above. Patient SEL has since had a reduction in peripheral adenopathy, resolution of low grade fevers and malaise and disappearance of SSF.

Fifty mls of venous blood obtained from patient SEL was heparinized to prevent clotting of red blood cells (5 units sodium heparin) and was used as a source of PBMC to isolate the T cells therefrom. The PBMC were isolated from the heparinized blood by Ficoll-Hypaque density gradient centrifugation (d=1.077) of whole heparinized blood diluted 1:1 (volume/volume) with 0.85% NaCl, 0.15M sodium phosphate buffer at pH 7.4 (hereinafter "PBS") at 900×g for 20 minutes at 25° C. The PBMC were found at the interface between the PBS and Ficoll-Hypaque layers. Next, the PBMC fraction was collected and incubated with sheep erythrocytes (E-rosette) for 45 minutes at 4° C. The sheep erythrocytes had been pretreated with 1.0% by weight neuraminidase prior to incubation with the PBMC fraction. The resulting sedimented pellet was dissolved in 5.0 ml of PBS and subjected to density gradient centrifugation in Ficoll-Hypaque as discussed above. The resulting E-rosette+ fraction, i.e., the cell pellet, was then subjected to lysis with 0.45M $NH_4Cl$ in 0.1M Tris Base in order to separate the sheep erythrocytes from the T cells. The resulting E-rosette− fraction, i.e., those cells at the interface of the PBS and Ficoll-Hypaque layers, were removed, washed with PBS and are hereinafter referred to as "non-T cells".

The resulting T cells were then incubated at 37° C. in a 95% air/5% $CO_2$ humidified atmosphere with 5.0% non-T cells, i.e., B cells plus monocytes, from the same patient, in the presence of 10 μg/ml of concanavalin A for 72 hours at a cell concentration of $1 \times 10^6$ T cells per ml of culture medium (RPMI 1640+10% fetal bovine serum) so as to ultimately increase fusion efficiency. The non-T cells had been pre-irradiated with 3000 rads of gamma-irridation prior to incubation with the T cells to prevent cell division of non-T cells. After this incubation, the cells were washed three times with PBS to remove the concanavalin A.

B.

T Cell Line

KE 37.3.2 was the T cell line employed in this example. KE 37.3.2 is the product of the mutagenization of the human T cell acute lymphoblastic leukemia line, i.e., KE 37 (see Mayer, L., Fu, S. M. and Kunkel, H. G., *J. Exp. Med.* 156:1860 (1982)) and the selection for HAT sensitivity. Both the leukemia cell line, KE 37, and the mutagenized T cell line, KE 37.3.2, are well known and available having been widely disseminated throughout the world.

C.

Fusion of T Cell with T Cell Line

The fusion of the T cells from patient SEL, obtained as described in Section A above, with KE 37.3.2, described in Section B above, was conducted as follows:

$2 \times 10^7$ stimulated T cells, isolated as described in Section A above, were pelleted with $1 \times 10^7$ KE 37.3.2 cells. Pellets were resuspended in 42% by volume polyethylene glycol (molecular weight 1000) and centrifuged at $150 \times g$ at 25° C. for 8 min. The cells were washed free of polyethylene glycol with RPMI 1640 anc cultured in 96-well, flat-bottomed microwell test plates at a concentration of $1 \times 10^5$ KE 37.3.2+T cells per well. Fused cells were cultured in culture medium (A) comprising RPMI 1640, 20% fetal bovine serum, 2 units/ml penicillin, 2 µg/ml streptomycin, 2 mM glutamine, $10^{-4}$M hypoxanthine and $1.6 \times 10^{-5}$M thymidine. After 24 hours of incubation at 37° C., $3 \times 10^{-8}$M aminopterin was added to culture medium (A) so as to select for hybridomas, i.e., HAT-resistant cells. After 2-3 weeks in culture medium (A) plus $3 \times 10^{-8}$M aminopterin, and feeding with the same culture medium every 3 days, growth-positive wells were transferred out of the aminopterin supplemented culture medium (A) and into 24-well flat-bottomed macrowell test plates in the presence of culture medium (A). With continued growth, the cultures were grown in RPMI 1640 plus 10% fetal bovine serum in 25-cm$^2$ flasks and cell-free supernatants were obtained and tested for functional (i.e., immunosuppressive) activity in vitro as described in more detail below.

D.

Cloning of Hybridomas

The cultures obtained above (hereinafter designated serially as "SK 1", "SK 2", etc.) were diluted in culture medium comprising RPMI 1640 plus 10% fetal bovine serum so that 0.2 ml gave an average of 0.33 cells per microwell test plate. These plates were incubated for 4 weeks at 37° C., and growth positive wells (clones at 95% confidence limits by Poisson analysis) were tested for immunosuppressive activity as discussed in more detail below.

E.

Identification of Hybridomas

Hybridomas were identified by demonstration of shared HLA class I allodeterminants between patient SEL (HLA/A1, Aw29/Bw35,B51/Cw4) and KE 37.3.2 (HLA-All,A30/B35,B44/Cw4) using the procedures, as described by Staff, NIAID in *Manual of Tissue Typing Technique* (NIH, Bethesda, MD) pp. 69-80 (1976).

The hybridomas were further characterized by using reagents for a panel of standard T cell markers (see Laurence, J.,/*Dis. Month.* 30:1 (1984). The hybridomas retained the membrane antigen profile of the parent line KE 37.3.2, detected by indirect immunofluorescence: 75% Leu-3a+ (helper-inducer T cell subset); 0% Leu-2a+ (suppressor-cytotoxic T subset); 0% Leu-4+ (mature pan-T cell marker); >95% OK T10+; and 0% HLA-DR+.

Neither the hybridoma cell lines nor KE 37.3.2 expressed human T cell leukemia virus type I or II (hereinafter "HTLV") product as detected by indirect intracellular immunofluorescence staining with a monoclonal antibody directed against HTLV core protein p19 (see Gallo, R. C., et al, *Science*, 220:865 (1983)).

F.

Immunosuppressive Activity In Vitro

1. Spontaneous and pokeweed mitogen-derived polyclonal immunoglobulin production FIG. 1 shows supernatant activities from initial uncloned growth positive wells (see Section C above) based upon their ability to affect T cell-dependent immune responses, i.e., pokeweed mitogen driven polyclonal immunoglobulin production by PBMC obtained from normal patients, i.e., patients without AIDS in a reverse hemoloytic plaque forming cell (hereinafter "PFC") assay. More specifically, after 24 hours, supernatants were obtained from cultures of $1 \times 10^6$ T cell hybridomas maintained in 1.0 ml RPMI 1640+10% fetal bovine serum at 37° C. in a 95% air/5% $CO_2$ humidified atmosphere. The supernatants were added, at a 1:9 final dilution (volume/volume), to $3 \times 10^5$ normal PBMC in 0.3 ml RPMI 1640+10% fetal bovine serum per microwell, to a 96-well, flat bottomed test plate together with a 1:150 dilution (volume/volume) of a 1.0% by weight solution of pokeweed mitogen (obtained from *Phytolacca americana*) in distilled water. The contents of duplicate wells were harvested after 6 days of culturing at 37° C. and PFC were determined by a reverse hemolytic plaque assay as described in Laurence, J., Gottlieb, A. B. and Kunkel, H. G., *J. Clin. Invest.* 72:2071 (1983).

The data in FIG. 1 are expressed at the percent inhibition of PFC in the absence of factors. Any enhancement of PFC is designated by * in FIG. 1, with the percent of enhancement shown in parentheses. As FIG. 1 demonstrates, supernatants from KE 37.3.2 had no PFC inhibiting effect, 9 out of 22 SK hybridoma derived supernatants gave significant, i.e., greater than 25%, constitutive inhibition of PFC, 2 out of 22 SK hybridoma derived supernatants gave enhanced PFC, i.e., greater than 25% increase of PFC and 11 out of 22 SK hybridoma derived supernatants revealed no significant activity.

Select supernatants were re-examined following 48 hours of incubation at a 1:2 dilution (volume/volume) in RPMI 1640+10% fetal bovine serum with $1.5 \times 10^5$/ml monocytes, in order to attempt to induce suppressor factors in inactive hybrid clones. The monocytes were prepared as described in Crow, M. K. and Kunkel, H. G., *Clin. Exp. Immunol.* 49:338 (1982). Two hybridomas, i.e., SK 8 (ATCC No. HB8585) and SK 10, which formerly revealed no significant suppression, evidenced marked inhibition of immunoglobulin synthesis (see FIG. 1). In no instance did pre-incubation of hybridoma supernatants with monocytes remove constitutive inhibitory activity.

In agreement with the effector profile of SSF obtained from T cell-monocyte interactions in patients with ARC or AIDS, constitutive hybridoma SK 7 (ATCC No. HB8584) and "induced" hybridoma SK 8/monocyte supernatants, i.e., supernatants from SK 8 hybridoma in the presence of monocytes, were noncytotoxic, as determined by supravital dye exclusion in 6-day pokeweed mitogen driven indicator cultures (see Laurence, J., Gottlieb, A. B. and Kunkel, H. G., *J. Clin. Invest.* 72:2071 (1983)).

Figure 2:
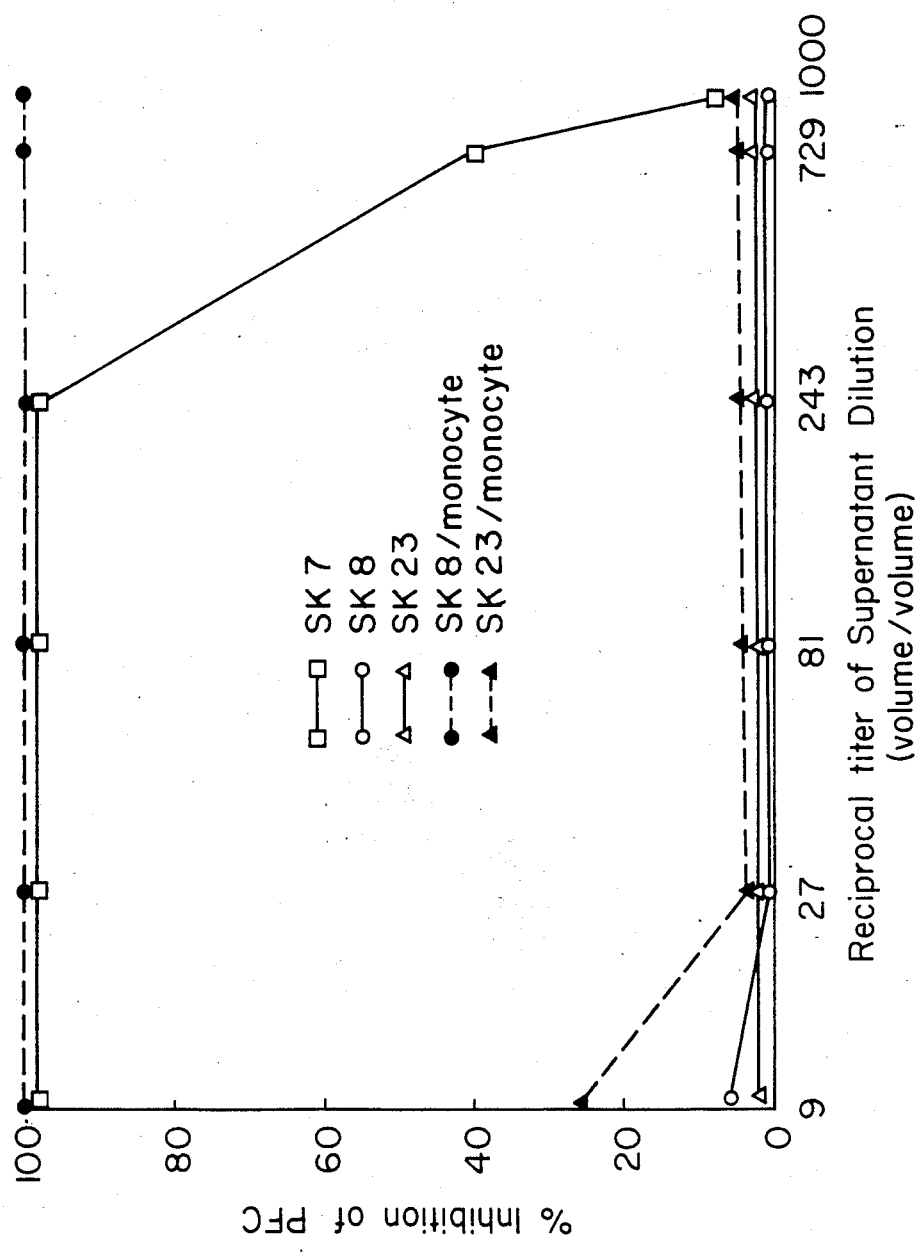
FIG. 2 illustrates dose-response curves for SSF obtained from T cell hybridomas of the present invention.

Dilution curves for supernatants obtained from hybridomas SK 7 and SK 8, pre- and post monocyte incubation, are shown in FIG. 2, wherein the data are expressed as percent inhibition of PFC in 6 day pokeweed mitogen driven indicator cultures in the reverse hemolytic plaque assay carried out as described above. Titers of T cell hybridoma derived SSF were found to be equivalent to or greater than that obtained from unstimulated PBMC isolated from patient SEL (titer 1:1000).

Figure 3:
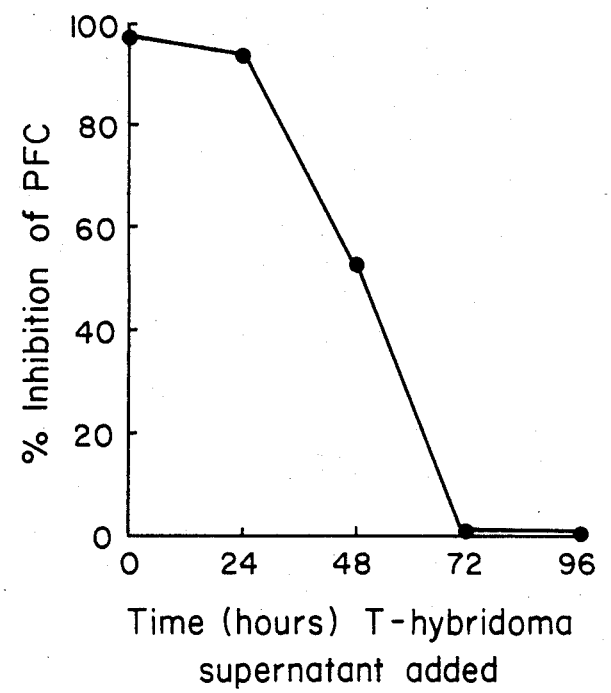
FIG. 3 illustrates the kinetics of SSF obtained from T cell hybridomas of the present invention in suppression of T cell-dependent polyclonal immunoglobulin synthesis.

FIG. 3 illustrates the kinetics of SSF obtained from T cell hybridomas of the present invention in the suppression of T cell-dependent polyclonal immunoglobulin synthesis. In FIG. 3, T cell hybridoma derived supernatants were added at a 1:9 final dilution (volume/volume) to pokeweed mitogen driven indicator cultures at varying times after culture initiation. The contents of each culture were harvested on day 6 and evaluated in the reverse hemolytic plaque assay as described above, with results expressed as percent inhibition of PFC.

Corresponding to the spontaneous SSF described in Laurence, J., Gottlieb, A. B. and Kunkel, H. G., *J. Clin. Invest.* 72: 2071 (1983), hybridoma SK 7 and SK 8/monocyte derived factors inhibited pokeweed mitogen driven immunoglobulin synthesis only if introduced within the first 48 hours of culture initiation (see FIG. 3). This indicates that SSF is non-cytotoxic and that it is able to disrupt differentiation of B cells to plasmacytes during the critical period at which regulatory cell helper activity is maximal (see Heijnen, C. J., Uytdehaag, F., Pot, C. H. and Balleux, R. E., *J. Immunol.* 126: 497 (1981)).

The cellular site of action of T cell hybridoma derived SSF was further examined using B cell enriched indicator populations activated with Epstein-Barr virus, a helper T cell-independent polyclonal mitogen, as described in Laurence, J., Gottlieb, A. B. and Kunkel, H. G., *J. Clin. Invest.* 72: 2071 (1983)). The results demonstrated that these supernatants had no effect on T cell-independent antibody production in normal B cells. These results further demonstrate that SSF is different from the concanavalin A stimulated soluble immunoresponse suppressor of mice (see Aune, T. M. and Pierce, C. W., *J. Immunol.* 127: 368 (1981)).

Restriction of SSF activity to T cells was demonstrated by absorption experiments as described in more detail below. Purified populations of normal E-rosette+ T cells, or non-T cells prepared as described in Laurence, J., Gottlieb, A. B. and Kunkel, H. B., *J. Clin. Invent.* 72: 2071 (1983), were incubated with hybridoma SK 7, SK 8 or SK 8 /monocyte derived supernatants for 4 hours at 37° C. More specifically, $2 \times 10^7$ cells were incubated with 1.0 ml of hybridoma derived supernatants at 37° C. for 4 hours with constant agitation. Then, the supernatants were collected by centrifugation at $900 \times g$ at 25° C. for 10 minutes, and added, at a 1:9 final dilution (volume/volume), to pokeweed mitogen driven incubator cultures as described above. Duplicate microwells were harvested on day 6 and the number of PFC were determined in the reverse hemolytic plaque assay as described above. The results in Table 1 below show that SSF activity in the SK 7 and SK 8/monocyte supernatants were diminished by pre-absorption with normal T cells, whereas its activity did not change following absorption with other immune cells subsets, i.e., non-T cells. KE 37.3.2 supernatants were unaffected by these pre-absorptions.

TABLE 1

Effect of Absorption of T Cell Hybridoma Derived Factors With Immune Cell Subpopulations on Suppressor Activity

| Supernatant Added | Pre-Absorption with: | Polyclonal Ig Synthesis: PFC/$10^6$ B cells (% inhibition PFC) |
|---|---|---|
| Medium | — | 9975 (—) |
| Medium/monocyte | — | 9310 (6.7) |
| SK 7 | — | 0 (100.0) |
| SK 7 | non-T cells | 0 (100.0) |
| SK 7 | T-cells | 7382 (26.0) |
| SK 8 | — | 6650 (33.3) |
| SK 8 | non-T cells | 7980 (20.0) |
| SK 8 | T cells | 7714 (22.7) |
| SK 8/monocyte | — | 0 (100.0) |
| SK 8/monocyte | non-T cells | 0 (100.0) |
| SK 8/monocyte | T cells | 3390 (60.0) |

The results in Table 1 above demonstrate that simple release of a pre-formed monokine under the influence of SK 8 derived supernatants is unlikely, as 4-hour incubation of SK 8 derived supernatant with non-T cells proved inadequate to produce SSF (see Table 1), which appears at about 12 hours of incubation and is maximal at 48–72 hours.

These results in Table 1 above also demonstrate that SSF, secreted directly by the T cell hybridomas of the present invention or as the product of a collaboration with normal monocytes, specifically suppress T cell-dependent immunoglobulin production and proliferative responses via a direct interaction with T cells or T cell products. Although the exact mechanism of SSF activity is not at present completely understood, since both SSF derived from AIDS patients and the SSF derived from T cell hybridomas of the present invention must be present during the initial 48 hours of the pokeweed mitogen driven PFC system, i.e., the period during which maximal helper factor activity is observed (see Heijnen, C. J., Uytdetlang, F., Pot, C. H. and Balleux, R. E., *J. Immunol.* 126: 497 (1981)). SSF may block lymphokine synthesis, secretion, or receptor function.

Data with hybridoma SK 8 indicated a two-step mechanism for the production of the SSF. Certain T cell hybridomas, like T cells from AIDS patients, may recruit a second population of cells with the characteristics of monocytes in the inhibition of T cell-dependent immune responses. The afferent limb of suppressor activity in human diseases and in experimental animal systems may involve serveral pathways linked by T cell-monocyte collaborations. Production of non-specific inhibitory factors by T cells from mice (see Deepe, Jr., G. S., Watson, S. R. and Bullock, W. E., *J. Immunol.* 132: 2064 (1984)) and man (see Stobo, J. D., *J. Immunol.* 119: 918 (1977)) with systemic mycoses in dependent upon substances liberated from monocytes of normal or infected individuals.

2. T cell blastogenic response to antigen

Lectin-free supernatants from patients with ARC or AIDS have also been shown to inhibit antigen-induced T cell proliferation (see Laurence, J., Gottlieb, A. B. and Kunkel, H. G., *J. Clin. Invest.* 72: 2071 (1983)) and blastogenic activity of normal T cells to various mitogens. Both SK 7 and SK 8/monocyte derived supernatants were capable of depressing tetanus toxoid mediated T cell mitogenesis of PBMC from pre-sensitized normal individuals as well as T cell responses to optimal concentrations of concanavalin A, pokeweed mitogen and phytohemagglutinin (75% inhibition at a 1:100 dilution (volume/volume)) as shown in Table 2 below, for phytohemagglutinin.

TABLE 2

| Supernatant Tested | Supernatant Dilution (vol./vol.) | Proliferative T Cell Response* | |
|---|---|---|---|
| | | Counts/minute | % Suppression |
| Medium | — | 160165 ± 5864 | — |
| SK 7 | 1:9 | 3179 ± 1169 | 98.0 |
| SK 7 | 1:27 | 15234 ± 1471 | 90.5 |
| SK 7 | 1:81 | 52942 ± 6935 | 67.0 |

*Representing the proliferative capacity of normal T cells stimulated by T cell mitogen phytohemagglutinin.

G. Comparison of SSF From AIDS Patients With SSF Derived From the Hybridomas of the Present Invention To determine that the hybridomas of the present invention secreted SSF comparable to that secreted by T cells from AIDS patients, the SSF's were compared. The physiochemical properties of SSF from the supernatants of hybridomas of the present invention were found to be similar to that of the SSF from AIDS patients and include: greater than 50% elimination of activity upon heating for 60 minutes at 56° C. or with the addition of $3 \times 10^{-5}$ M 2-mercaptoethanol on initiation of pokeweed mitogen driven target cells. Further, both products are resistant to 50 mM L-rhamnose and 50 mM N-acetyl-D-glucosamine, which are two sugars reported to reverse the inhibitory effects of suppressor factors produced by concanavalin A stimulated PBMC and acting on immunoglobulin production at the B cell level (see Fleisher, T. A., Greene, W. C., Blaese, R. M. and Waldmann, T. A., *J. Immunol.* 126: 1192 (1981) or on mitogen and antigen induced T cell proliferation (see Greene, W. C., Fleisher, T. A. and Waldmann, T. A., *J. Immunol.* 126: 1185 (1981)), respectively.

The apparent size of the T cell hybridoma derived SSF was determined by molecular weight sieve chromatography on Sephadex S-200. A major peak of suppressor activity for pokeweed mitogen induced PFC was detected at approximately 47,000 daltons, migrating between ovalbumin (45,000) and albumin (67,000).

Hybridomas SK 7 and SK 8 have remained in continuous culture, with two subclonings for 10 months with persistence of activity. Hybridoma SK 10 no longer expresses an active lymphokine, despite repetitive cloning.

SK 7, SK 8, HM 1 and HM 2 have also been stored in plastic NUNC tubes at −80° C. in liquid nitrogen tanks. The hybridomas are prepared for controlled freezing, utilizing a Honeywell Cryo-Med Model No. 972 freezing apparatus, by suspension of $100 \times 10^6$ cells in 1.8 ml of RPMI 1640 plus 20% fetal bovine serum plus 10% dimethyl sulfoxide per NUNC tube. Greater than 90% viability is routinely obtained upon thawing of these cells. The SSF activity of supernatant from the above hybridomas remains unchanged after the freeze-thaw process.

SK 7 can also be cultured in a medium comprising amino acids, glucose, sodium pyruvate, transferrin, insulin, 1.0% bovine serum albumin, but lacking whole serum (HB 103 liquid medium, Hana Media, Inc., Berkeley, Calif.). This medium is capable of supporting full SSF production, and thus is useful for isolation of large amounts of SSF in cells grown in suspension cultures, with a view to isolation of such SSF for in vivo clinical use. The bovine serum albumin can be separated from these cultures prior to intravenous or intramuscular injection of SSF utilizing well-known physical (albumin binding columns) or chemical (salt precipitation) techniques.

H. Immunosuppressive Activity In Vivo

The SSF from the hybridomas of the present invention can be employed in vivo in a manner similar to the use of other T cell or T cell hybridoma products to treat disease, e.g., using a mouse model as described in Krakauer, R. S., Strober, W., Rippeon, D. L, and Waldmann, T. A., *Science* 196: 56 (1977) and Ginsberg, C. H., Dambrauskas, J. T., Whitaker, R. B., Falchuk, Z. M. and Greene, M. I., *J. Immunol.* 132: 203 (1984). Furthermore, it is well known that the in vivo activity of most immunosuppressive drugs in mice is equivalent to that in humans as reviewed in Moller, G., Ed., *Immunol. Rev.*, 65: 5 (1982). Thus, the in vivo activity of SSF from the T cell hybridomas of the present invention demonstrated in mice, as described below, is considered to correlate with activity in humans. Hybridomas SK 7 and SK 8 and SK 8/monocyte supernatants have the capacity to induce an immunodeficiency state in an in vivo murine system, characterized by marked suppression of antigen-specific antibody production in BALB/c mice administered these factors intraperitoneally (hereinafter "I.P.") as described in more detail below.

0.5 ml of a T cell hybridoma of the present invention or control derived supernatant was subjected into 8-week old male BALB/c mice on days: −3, −2, −1, 0 and 1–5. On day 0, $1 \times 10^9$ sheep red blood cells in 0.5 ml of normal saline were administered I.P. At the end of day 5, each mouse was sacrificed, peripheral blood was obtained for total serum IgM immunoglobulin determinations, and the spleens of each animal were recovered for evaluation of sheep red blood cells-specific IgM antibody (hereinafter "IgM-anti SRBC Antibody") production in a standard hemolytic plaque assay as described in Mishell, B. B. and Shiigi, S. M., Eds., *Selected Methods in Cellular Immunology*, (W. H. Freeman and Co., San Francisco (1980)). No supernatant had any direct cytotoxic effect, as demonstrated by the total number of cells obtained per spleen. No supernatant had any effect, in this brief period, on the total serum IgM antibody levels, as shown in Table 3 below. These results further demonstrate that SSF is distinguishable from the murine suppressor factors having in vivo activity described by Krakauer, R. S., Strober, W., Rippeon, D. L. and Waldmann, T. A., *Science* 196: 56 (1977).

TABLE 3

EFFECT OF I.P. ADMINISTERED T CELL HYBRIDOMA SUPERNATANTS ON TOTAL SERUM IgM LEVELS

| SUPERNATANT TESTED | TOTAL SERUM IgM*: MEAN (RANGE) in mg/ml |
|---|---|
| SK 7 | 4.16 (2.2–8.5) |
| SK 8 | 6.49 (0.74–16.3) |
| SK 23 | 2.05 (1.3–2.8) |
| KE 37 | 4.67 (1.1–11.0) |
| Monocyte | 1.97 (1.2–2.7) |
| SK 8-monocyte | 4.72 (1.1–11.0) |

*IgM levels measured by radioimmunoassay as described in Mishell, B.B., Shiigi, S.M., Eds., Selected Methods in Cellular Immunology (W. H. Freeman, San Francisco 1980).

Furthermore, only hybridomas SK 7, SK 8 and SK 8/monocyte, and not any of the control supernatants (i.e., KE 37, monocyte, or SK 23, a clone which did not secrete SSF) had any significant effect on antigen-specific plaques as shown in Table 4 below.

sarcoma and *Pneumocystis carinii* pneumonia, who has subsequently died of AIDS. The T cells were isolated from the peripheral blood of patient HOLC and stimu-

TABLE 4

Effect of I.P. administered T Cell Hybridoma Supernatants On IgM-anti-SRBC Antibody Production

| Group | Supernatant injected | No. of mice/group | Mean ± SD PFC/$10^6$ spleen cells | p* | Mean ± SD PFC/spleen | p* | Mean ± SD total splenocytes ($\times 10^{-6}$) | p* |
|---|---|---|---|---|---|---|---|---|
| 1. | KE 37 | 9 | 599.6 ± 152 | — | 103,438 ± 26,573 | — | 178.4 ± 49 | — |
| 2. | Monocyte | 6 | 722 ± 339 | NS | 127,083 ± 34,311 | NS | 197.3 ± 62 | NS |
| 3. | SK 23 | 3 | 499.3 ± 157 | NS | 78,738 ± 27,882 | NS | 159.4 ± 28 | NS |
| 4. | SK 7 | 9 | 396.3 ± 151 | 0.01 | 73,467 ± 35,013 | 0.059 | 189.9 ± 63 | NS |
| 5. | SK 8 | 8 | 249.1 ± 195 | 0.001 | 46,518 ± 38,596 | 0.004 | 180.9 ± 40 | NS |
| 6. | SK 8/monocyte | 8 | 354.6 ± 179 0.046+ | 0.009 | 66,878 ± 26,576 0.006+ | 0.01 | 206.3 ± 67 NS+ | NS |

NS = not significant
* = statistically compared with KE 37
+ = statistically compared with monocyte supernatant injection I. Relationship of SSF to Known T Cell Products Utilizing normal PBMC of divergent HLA-DR allotypes, SSF function proved not to be genetically constrained. Thus, SSF derived from SK 7 or SK 8 can block the immune reactivity of T cells obtained from donors of representative examples of HLA-D and HLA-DR allotypes, e.g., HLA-D/DR types, 1, 2, 3, 4, 5, 6, and 7.

Furthermore, indomethacin (1–10 mg/ml) employed as anti-prostaglandin, did not affect SSF activity. Thus, these results demonstrate that SSF is not a prostaglandinlike product.

In addition, sheep anti-human alpha interferon (Interferon Sciences, Inc., New Brunswick, N.J.) (1–10 units/culture), and a murine monoclonal anti-human gamma interferon antibody obtained from Dr. B. Y. Rubin, The New York Blood Center (1–10 units per culture), did not affect SSF activity. Alpha and gamma interferons are soluble factors which are known to be able to inhibit immune response both in vitro and in vivo. Thus, these results demonstrate that SSF is not an interferon-like product. Further, SSF obtained from hybridoma SK 7 and SSF from hybridoma SK 8/monocytes had no influence on a cytopathic effect-inhibition assay for gamma interferon, using vesicular stomatitis virus and WISH cells (see Murray, H. W., Rubin, B. Y., Masur, H. and Roberts, R. B., *N. Engl. J. Med.* 310: 883 (1984); Rubin, B. Y., Bartal, A. H., Millet, S. K., Hirshaut, Y. and Feit, C., *J. Immunol.* 130: 1019 (1983)). These results further demonstrate that SSF is not an interferon-like product.

Supernatants from hybridoma SK 7 had no effect on the synthesis of interleukin 2 by a clone of the Jurkat human T cell leukemia line, on the utilization of this lymphokine by an interleukin 2 dependent T cell clone, or on peroxide-mediated macrophage cytotoxicity. It is improbable that the immunosuppressive effect observed is directly mediated by LAV particles, since addition of infectious LAV on initiation of a T cell proliferative PFC assay had no effect on the ultimate response measured. Thus, these results demonstrate that SSF activity is not dependent upon an infectious virus which might have been present in the original hybridoma.

EXAMPLE 2

In this Example, concanavalin A stimulated T cells were obtained from patient HOLC who was diagnosed as an AIDS patient by the criteria discussed above. Patient HOLC was a homosexual male with Kaposi's lated as described in Example 1 for patient SEL. The isolated T cells were then fused to a widely available T cell line, MOLT 4, using the same procedures as described in Example 1 above except a rosetting technique, rather than selective medium, was employed to select a series of "HM" hybridomas, using procedures as detailed in Mayer, L., Fu, S. M. and Kunkel, H. B., *J. Exp. Med.*, 156: 1860 (1982 ). More specifically, after fusion of stimulated T cells to MOLT 4 in the presence of polyethylene glycol, the entire cell pellet was resuspended in RPMI 1640 and incubated in OKT4 antibody (Ortho Pharmaceuticals, Raritan, N.J.) as described in Mayer, L., Fu, S. M., Kunkel, H.G., *J. Exp. Med.* 156: 1860 (1982). The mixture was then rosetted with goat-anti-mouse-immunoglobulin-coated ox erythrocytes, coated by a chromium chloride technique (see Chiorazzi, N., Fu, S. M., Kunkel, H. G., *Clin. Immunol. Immunopathol.* 15: 301 (1980)). The rosetted cells were then subjected to Ficoll-Hypaque density gradient centrifugation. Cells isolated at the interface of this gradient were discarded. Pelleted, E-rosette+ cells were treated with NH$_4$Cl/TRIS as described in Example 1. The remaining cells following erythrocyte lysis represented the OKT8+/OKT4+ T cell hybrids, with the OKT4 moiety having been contributed by the T cells from patient HOLC and the OKT8 moiety having been contributed by MOLT 4. Supernatants from HM 1 (ATCC No. HB8586) and HM 2 (ATCC No. HB8587) exhibited SSF activity equivalent in a PFC assay to that of the supernatants from hybridoma SK 7 as shown in Table 5 below. However, HM 1 and HM 2 do not have as great a capacity to produce SSF as do SK 7 and SK 8. Further, HM 1 and HM 2 have not been cloned by limiting dilutions.

TABLE 5

Effect of HM 1 and HM 2 T Cell Hybridoma Supernatants On Pokeweed Mitogen Induced Polyclonal Antibody Production

| | Immunoglobulin Production | |
|---|---|---|
| Supernatant Tested* | Mean PFC/slide | % Suppression |
| Medium | 265 | — |
| HM 1 | 9.5 | 99.2 |
| HM 2 | 20 | 92.5 |

*1:9 dilution (volume/volume)

While the invention has been described in detail and with reference to specific embodiments thereof, it will be apparent to one skilled in the art that that various changes and modifications can be made therein without departing from the spirit and scope thereof.

I claim:

1. A human T cell hybridoma comprising: the fusion product produced by the process comprising:
   (A) fusing:
      (i) a T cell from a patient with acquired immune deficiency syndrome-related complex or acquired immune deficiency syndrome, wherein said T cell secretes a soluble suppressor factor capable of specifically inhibiting T cell-dependent responses while leaving other immune functions intact, and
      (ii) a human T cell line,
   followed by
   (B) selecting from the product of (A) a human T cell hybridoma which secretes a soluble suppressor factor capable of specifically inhibiting T cell-dependent responses while leaving other immune functions intact.

2. The human T cell hybridoma of claim 1, wherein said T cell (i) is from a patient with acquired immune deficiency syndrome-related complex.

3. The human T cell hybridoma of claim 1, wherein said T cell (i) is from a patient with acquired immune deficiency syndrome.

4. The human T cell hybridoma of claim 1, wherein said T cell line (II) is selected from the group consisting of KE 37.3.2, KE 37, MOLT 4, MOLT 3, CCRF-CEM, HuT 78 and Jurkat 3.

5. The human T cell hybridoma of claim 1, wherein said human T cell hybridoma is SK 7 having the identifying characteristics of ATCC No. HB8584.

6. The human T cell hybridoma of claim 1, wherein said human T cell hybridoma is SK 8 having the identifying characteristics of ATCC No. HB8585.

7. The human T cell hybridoma of claim 1, wherein said human T cell hybridoma is HM 1 having the identifying characteristics of ATCC No. HB8586.

8. The human T cell hybridoma of claim 1, wherein said human T cell hybridoma is HM 2 having the identifying characteristics of ATCC No. HB8587.

* * * * *